US006967028B2

(12) United States Patent
Dulieu et al.

(10) Patent No.: US 6,967,028 B2
(45) Date of Patent: Nov. 22, 2005

(54) PROLONGED RELEASE MICROSPHERES FOR INJECTABLE ADMINISTRATION

(75) Inventors: Claire Dulieu, Angers (FR); Joël Richard, Longue (FR); Jean-Pierre Benoit, Avrille (FR)

(73) Assignees: Mainelab, Angers (FR); Laboratoires des Produits Ethiques Ethypharm, Houdan (FR)

( * ) Notice: Subject to any disclaimer, the term of this patent is extended or adjusted under 35 U.S.C. 154(b) by 360 days.

(21) Appl. No.: 09/873,271

(22) Filed: Jun. 5, 2001

(65) Prior Publication Data

US 2004/0071785 A1 Apr. 15, 2004

Related U.S. Application Data

(60) Provisional application No. 60/222,789, filed on Jul. 31, 2000.

(51) Int. Cl.$^7$ .............................. A61K 9/50; B32B 15/02
(52) U.S. Cl. ................... 424/501; 424/502; 428/402.21
(58) Field of Search ................................ 424/497, 498, 424/501, 502; 428/403, 402.21

(56) References Cited

U.S. PATENT DOCUMENTS

| | | | | | |
|---|---|---|---|---|---|
| 6,183,783 | B1 | * | 2/2001 | Benoit et al. ............... | 424/497 |
| 6,248,363 | B1 | * | 6/2001 | Patel et al. .................. | 424/497 |

FOREIGN PATENT DOCUMENTS

| | | |
|---|---|---|
| CA | 2214889 | 9/1997 |
| EP | 0 251 368 A1 | 3/1988 |
| EP | 0 257 368 A1 | 3/1988 |
| EP | 0 706 821 A1 | 4/1996 |
| WO | WO 96/28143 | 9/1996 |
| WO | WO 98/15348 | 4/1998 |

OTHER PUBLICATIONS

Ogawa et al., "A New Technique to Efficiently Entrap Leuprolide Acetate into Microcapsules of Polylactic Acid or Copoly (Lactic/Glycolic) Acid," Chem. Pharm. Bull. 36 (3) 1095–1103 (1988).
McGee et al., "Zero Order Release of Protein from Poly(D, L–lactide–co–glycolide) Microparticles Prepared Using a Modified Phase Separation Technique," J. of Controlled Rlease 34 (1995) 77–86.
Ruiz et al., "Influence of Average Molecular Weights of Poly(DL–Lactic Acid–Co–Glycolic Acid) Copolymers 50/50 on Phase Separation and in Vitro Drug Release from Microspheres," Pharmaceutical Research, vol. 7, No. 9, 928–934 (1990).
Hora et al., "Release of Human Serum Albumin From Poly(lactide–co–glycolide) Microspheres," Pharmaceutical Research, vol. 7, No. 11, 1190–1194 (1990).
Jalil et al., "Biodegradable Poly(lactic acid) and Poly(lactide–do–glycolide) Microcapsules: Problems Associated with Preparative Techniques and Release Properties," J. Microencapsulation, 1990, vol. 7, No. 3, 297–325.
Debenedetti et al., "Application of Supercritical Fluids for the Production of Sustained delivery Devices," Journal of Controlled Release, 24 (1993) 27–44.

* cited by examiner

Primary Examiner—Carlos Azpuru
(74) Attorney, Agent, or Firm—Burns, Doane, Swecker & Mathis, LLP

(57) ABSTRACT

The present invention provides microspheres intended to be administered by injection comprising a protein active ingredient and an agent coating the active ingredient intended to prolong its release, wherein they are free of any trace of organic solvent and they can be obtained according to a coating method involving bringing the active ingredient and the coating agent into contact, with stirring, in a supercritical fluid, said coating agent being soluble in this supercritical fluid.

26 Claims, 3 Drawing Sheets

PROLONGED RELEASE MICROSPHERES FOR INJECTABLE ADMINISTRATION

This application claims the right to priority under 35 U.S.C. § 119(e) to U.S. Provisional Patent Application No. 60/222,789, filed Jul. 31, 2000.

BACKGROUND OF THE INVENTION

The present invention relates to the field of microparticles intended to be administered by injection or by the subcutaneous or muscular route.

There is currently a need for prolonged-release pharmaceutical formulations intended for the administration of proteins by injection, which are free of any trace of organic solvents.

Intense efforts have to be made to develop efficient novel systems for the administration of proteins. All the conventional techniques for preparing controlled release injectable microparticulate systems, whether they be the preparation of microcapsules by the emulsion (oil/water)/solvent evaporation method (Hora et al., Pharm. Res., 7 (1990), 1190–1194; Jalil, R. et al., L. Microencapsulation, 7 (1990) 294–325), the coacervation method in organic phase (Ruiz et al., Pharm. Res., 7 (1990) 928–934; McGee, J. P. et al., J. Controlled Release, 34 (1995) 77–86) or by the double emulsion (water/oil/water)/solvent evaporation technique (Ogawa, Y et al., Chem. Pharm. Bull., 36 (1988) 1095–1103), lead to the use of organic solvents. These require steps for accurately controlling and measuring the levels of residual solvents in order to limit these levels and to avoid any harmful side effects on the patient. Furthermore, government authorities introduce strict standards for avoiding contamination of the environment with the organic solvents inherent to the methods of production and to limit or even eliminate the use of organic solvents in pharmaceutical compositions. Finally, in protein formulations, problems of denaturation induced by contact with solvents and undesirable phenomena of adsorption at solvents/water interfaces can occur.

BRIEF SUMMARY OF THE INVENTION

The subject of the present invention is microspheres intended to be administered by injection, comprising a protein active ingredient and an agent coating the active ingredient intended to prolong its release.

The microparticles according to the invention, containing a protein active ingredient, are distinguishable from the microparticles of the prior art by their matrix structure and by the absence of any trace of organic solvent.

The microparticles according to the invention are free of any trace of organic solvent and they can be obtained according to a coating method involving bringing the active ingredient and the coating agent into contact, with stirring, in a supercritical fluid, said coating agent being soluble in this supercritical fluid. The protein active ingredient is, for its part, insoluble in the supercritical fluid.

The mean size of the microparticles according to the invention is between 0.1 and 150 $\mu$m.

Their content of active ingredient is between 0.5 and 50% by weight, preferably between 3 and 20% by weight.

DETAILED DESCRIPTION OF THE INVENTION

Figure 1:
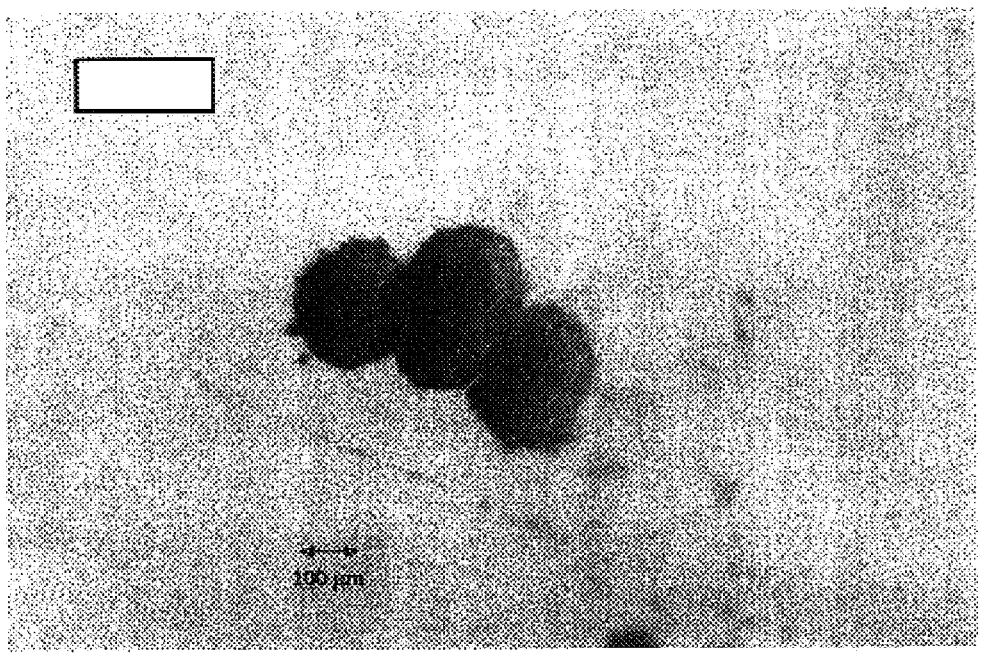
FIG. 1 is an optical micrograph of three microshperes obtained according to Example 1.
Figure 2:
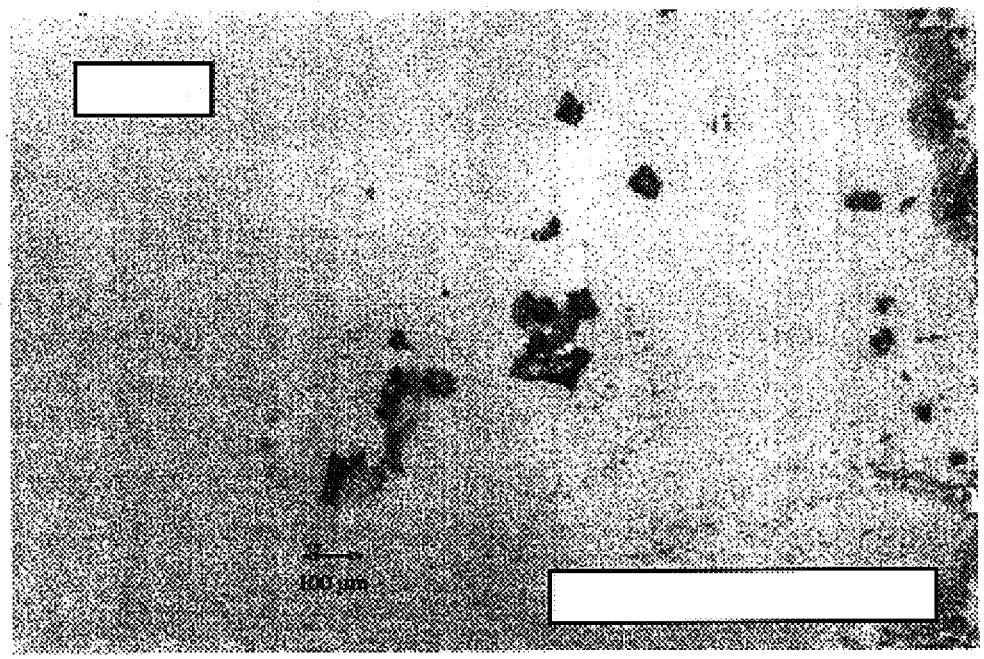
FIG. 2 makes it possible to demonstrate the matrix structure of the microspheres of FIG. 1. After addition of a few drops of a few drops of dichloromethane (solvent for the coating agent), about fifteen crystals of BSA (insoluble in dichloromethane) are visible.
Figure 3:
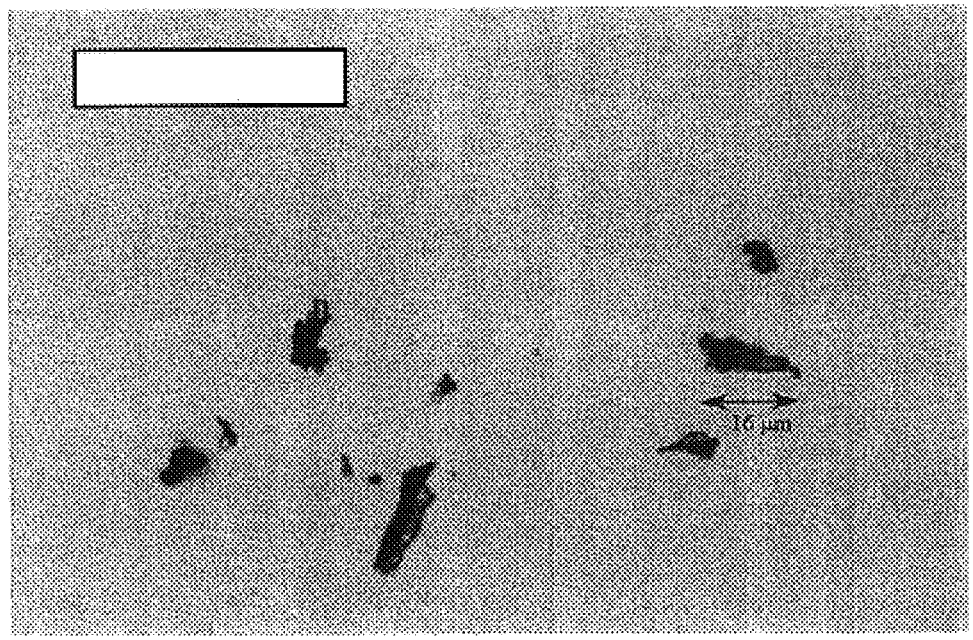
FIG. 3 is an optical micrograph of erythropoietin particles used in Example 2, before their coating.
Figure 4:
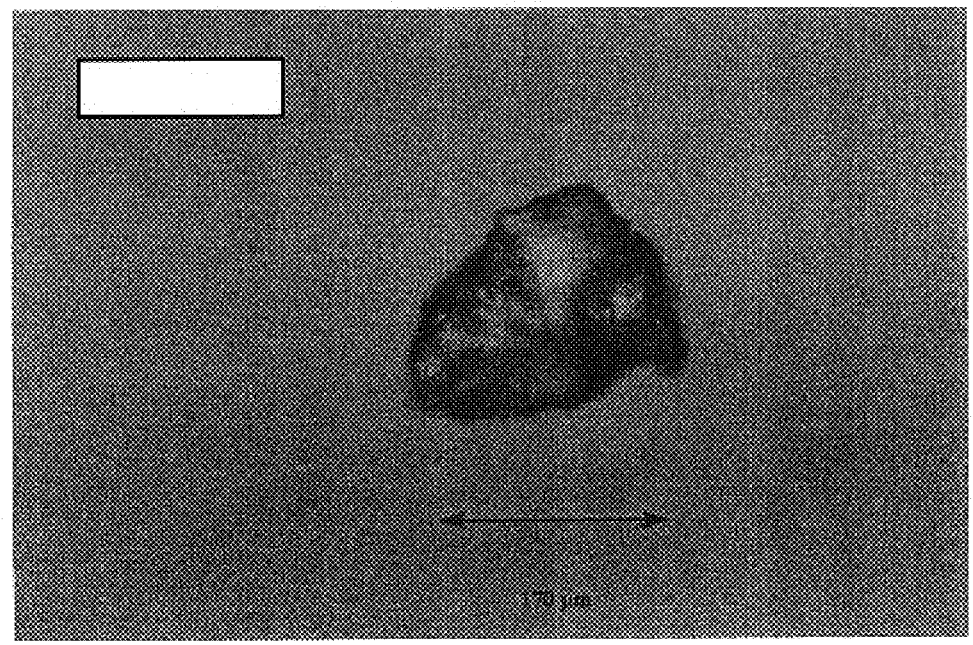
FIG. 4 is an optical micrograph of a microsphere containing particles of erythropoietin obtained according to Example 2.
Figure 5:
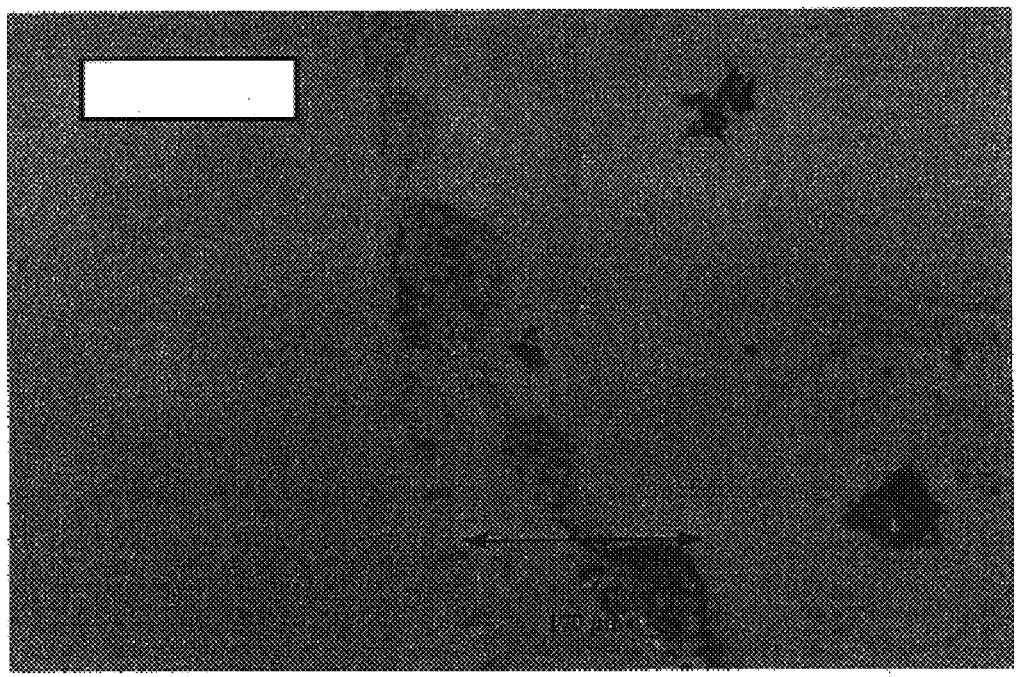
FIG. 5 makes it possible to demonstrate the matrix structure of the microsphere of FIG. 4. After addition of a few drops of dichloromethane (solvent for the coating agent), three crystals of erythropoietin are visible.

It has been demonstrated that the use of a method of preparing microparticles by a technique using a supercritical fluid and a coating agent soluble in this fluid makes it possible to obtain microspheres with advantageous properties.

Application EP 706,821 describes the coating of particulate active substances in the case where the coating agent used is soluble in supercritical $CO_2$. After solubilization in supercritical $CO_2$, the coating agent is brought into contact with the protein to be coated in a closed reactor, with stirring. Pressure and temperature modifications in the latter lead to desolvation of the coating agent and therefore to its precipitation over the active substance. This method does not involve either organic solvent or water, and is carried out at a relatively low temperature. More precisely, the particles of active substance are suspended in the supercritical $CO_2$, and then the coating agent is dissolved in the suspension. The pressure and/or the temperature are then decreased in a controlled manner so as to reduce the solubility of the coating in the supercritical fluid and to cause the deposition of the coating at the surface of the particles of active substance. The layer of coating may be monomolecular or may be up to 100 $\mu$m thick. The size of the encapsulated particles is between 20 nm and 500 $\mu$m. The coating is a fatty substance or a biodegradable polymer which is soluble in supercritical $CO_2$. The deposition of the coating is carried out between 30 and 80° C., between 70 and 250 bar for 30 minutes to 4 hours, with stirring.

The carrying out of the method according to the invention consists in suspending an active ingredient, with stirring, in a supercritical fluid containing at least one coating agent dissolved therein, and then in modifying the pressure and/or temperature conditions of the medium in order to bring about the coacervation of the particles, by desolvation of the coating agent around particles of active ingredient, that is to say to bring about the coacervation of the particles by physicochemical modification of the medium. This method leads to matrix microparticles containing several particles of protein active ingredient.

It has been discovered in the context of the present invention that by adapting the value of certain parameters of the method, in particular the content of active ingredient equivalent to the active ingredient/coating agent ratio, the mode of stirring, and the coating agent/supercritical fluid ratio, microparticles with advantageous properties and which have a matrix structure are obtained.

The supercritical fluid preferably used is supercritical $CO_2$ ($CO_2SC$), the typical initial operating conditions for this method are about 31 to 80° C. and from 75 to 250 $10^5$ Pa, although it is possible to use higher values of either of the two parameters or of both, provided of course that the higher values have no harmful or degrading effect on the active ingredient being coated, or on the coating agents.

This method involves suspending in an autoclave an active ingredient insoluble in the supercritical fluid, and then introducing into this autoclave the coating agent which is in the state of a solute in the supercritical fluid.

The pressure and/or the temperature are then modified so as to reduce the solubility of the coating agent in the fluid. Thus, the affinity of the coating agent for the active ingredient increases such that this coating becomes adsorbed around the active ingredient. Once this coating agent is deposited on the active ingredient, the autoclave is depressurized and the microparticles are recovered.

To carry out this method, the active ingredient to be coated is placed in an autoclave equipped with a stirrer and then the system is pressurized by introducing into the autoclave a fluid supplied under supercritical conditions. Finally, the coating agent(s) is (are) introduced into the autoclave and then the temperature and/or the pressure inside the autoclave is modified in a controlled and regulated manner so as to gradually reduce the solubility of the coating agent(s). When the solubility of this (these) coating agent(s) in the supercritical fluid decreases, it (they) precipitate(s) and the affinity of these agents for the surface of the active ingredient leads to their adsorption onto this surface. A variant of this method consists in placing the coating agent in the autoclave before introducing the active ingredient therein or alternatively in introducing the active ingredient therein and then a fluid capable of changing to the supercritical state. The pressurization of the autoclave in order to produce a supercritical fluid state will then cause the dissolution of the coating agent in said supercritical fluid.

The stirring speeds may vary between 200 and 1000 revolutions/min, preferably 450 rpm.

Such a stirring brings about the suspension of the active ingredient in the supercritical fluid when the latter is introduced. The supercritical conditions are brought about by a modification of the temperature and/or of the pressure inside the autoclave. Thus, the temperature of the autoclave is between 35 and 80° C., preferably between 35 and 45° C. and the pressure is between 100 and 250 $10^5$ Pa and preferably between 180 and 220 $10^5$ Pa. The coating agent is introduced into the autoclave at the same time as the supercritical fluid or alternatively after introduction of the supercritical fluid into the autoclave. In any case, to ensure good solubilization of the coating agent in the supercritical fluid, the system is maintained at equilibrium, with stirring, adequate concentration of active ingredient and of coating agent is established according to the microparticle desired and this equilibrium is kept stirring for about one hour. The temperature and the pressure are then varied at a sufficiently low speed to completely transfer the coating agent(s) in the supercritical fluid to the surface of the active ingredient and the system is depressurized in order to isolate the microparticles which are removed from the autoclave.

The concentration of coating agent in the supercritical fluid is preferably between 1.5 and 4.5 g/l, preferably equal to 2 g/l.

According to a preferred embodiment of the invention, a cylindrical insert is placed in the autoclave, and is screwed to the cover before closing. The supercritical fluid is preferably introduced through the top part of the insert after closing the autoclave.

This insert is advantageously equipped with two sinters allowing the inflow and outflow of the supercritical fluid. The insert is preferably provided with an annular sinter in its top part, and with a discoid sinter constituting the bottom of the said insert. The two sinters advantageously have a porosity less than the size of the microspheres which it is desired to prepare.

The insert makes it possible to recover the microspheres containing the active ingredient. At the end of the process, it is unscrewed and moved, optionally in a chamber containing an inert gas when the protein active ingredient is sensitive to moisture, and is inverted in order to recover the microspheres. It allows the use of an inert propellant gas to facilitate the recovery of the microspheres containing the active ingredient when said active ingredient is sensitive to moisture.

The coating agent entering into the composition of the microspheres of the invention, optionally chosen for carrying out their method of preparation, may be a biodegradable polymer or a fatty substance.

The coating agent is particularly chosen from biodegradable polymers and copolymers of α-hydroxycarboxylic acids, in particular homopolymers and copolymers of lactic and glycolic acids, more particularly PLA (Poly-L-lactide) and PLGA (Poly-Lactic-co-Glycolic Acid), poly(ε-caprolactone) and its derivatives, poly-(β-hydroxybutyrate), poly(hydroxyvalerate) and (β-hydroxybutyrate-hydroxyvalerate) copolymers, polymalic acid, amphiphilic block polymers of the polylactic acid-polyethylene oxide type, biocompatible polymers of the polyethylene glycol type, polyethylene oxides, block copolymers of the polyethylene oxide-polypropylene oxide type, polyanhydrides, polyorthoesters, poly-phosphazenes, and mixtures thereof.

These polymers, chosen to be effective coating agents, have a molar mass greater than $10^3$ g/mol, preferably greater than $2 \times 10^3$ g/mol and more particularly between $2 \times 10^3$ and $2 \times 10^5$ g/mol.

The polymer is chosen such that it is soluble in supercritical fluid, by adapting in particular the particle size, the crystallinity, the weight-average molecular mass, the chemical composition, the functionalization of the side and/or end groups and the acid value.

All these parameters are adjusted in order to obtain the desired solubility of the polymer in the supercritical fluid and/or to obtain the desired release profile for the protein active ingredient.

The coating agent is also chosen from fatty substances such as phospholipids, in particular phosphatidylcholine, phosphatidylglycerol, diphosphatidylglycerol, dipalmitoyl-phosphatidyl-choline, dioleyl-phosphatidylethanolamine, dioleyl-phosphatidylcholine, dimyristoyl-phosphatidylglycerol, or triglycerides, in particular $C_8$ to $C_{12}$ triglycerides, such as triglycerides of capric and caprylic acids, solid fatty acid esters, in particular $C_8$ to $C_{18}$ fatty acid esters such as ethyl palmitate, ethyl myristate, octyldodecyl myristate, preferably $C_8$ to $C_{12}$ fatty acid esters and mixtures thereof.

The coating agent may also be a mixture of one of the polymers and of one of the fatty substances mentioned above.

A particularly preferred coating agent in the context of the present invention is a Gélucire® (mixture of mono-, di- and triglycerides, of fatty acid esters and of polyethylene glycol).

According to a preferred embodiment, the coating agent is a GÉLUCIRE®, the temperature in the autoclave is of the order of 45° C., the pressure in the autoclave is of the order of 200 bar and the stirring speed is of the order of 450 rpm.

The protein active ingredient may be a protein or a peptide.

The proteins falling within the scope of the present invention are chosen from the parathyroid hormone related protein (parathyroid hormone related protein), growth hormone (GH), α-, β- or γ-interferons, α- or β-erythropoietin (EPO), granulocyte colony stimulating factor (GCSF), granulocyte macrophage colony stimulating factor (GMCSF), PACAP polypeptide (pituitary adenylate cyclase activating polypeptide), vasoactive intestinal peptide (VIP), thyrotropin releasing hormone (TRH), corticotropin releasing hormone (CRH), arginine vasopressin (AVP), angiotensin, insulin, somatotropin, the HBS antigen of the hepatitis B virus, plasminogen tissue activator, the coagulation factors VIII and IX, glucosylceramidase, sargramostim, lenograstin, filgrastin, interleukin-2, dornase-α, molgramostim, PEG-L-asparaginase, PEG-adenosin deaminase, hirudin, eptacog-α (human blood coagulation factor VIIa) and nerve growth factors (NGF, CNTF, BDNG, FGF, GDNF).

A particularly preferred protein in the context of the invention is erythropoietin, a glycosylated protein hormone which has a hematopoietic growth factor action. It is produced by genetic engineering under the name epoetin, and used clinically to maintain or raise the level of the patient's red blood cells. It is indicated in anemia cases, during hemodialysis in chronic renal insufficiency sufferers, in parallel with a chemotherapy, in HIV patients or before a surgical operation. The treatment requires at least three injections per week.

Another particularly preferred protein in the context of the invention is alpha-interferon. Its activity spectrum is very broad since it is used both for its antiviral, anticancer and immunomodulatory properties. It is in particular used for the treatment of hepatitis B, hepatitis C, some leukemias and Kaposi's syndrome. The treatment comprises three injections per week for 6 to 12 months.

Peptides, such as the derivatives of LHRH or of somatostatin, triptorelin, bombesin, calcitonin, parathyroid hormone, gastrin releasing peptide (GRP), luteinizing hormone releasing hormone (LHRH), growth hormone releasing factor (GRF), the peptide derivative Acetyl-Ser-Asp-Lys-Pro and amylin can also be used as active ingredient in the context of the present invention.

The size of the particles of protein active ingredient entering into the composition of the microspheres is between 20 nm and 60 μm, preferably between 15 and 50 μm.

EXAMPLE 1

Microspheres of GÉLUCIRE® 50/02 Containing the Model Protein Bovine Serum Albumin (BSA)

Materials 300 ml autoclave provided with an insert 180 ml in volume, which is porous (10 μm) at the top and at the bottom. An autoclave provided with a jacket for the regulation of temperature: circulation of silicone oil, heated or cooled by a thermostated bath. Stirring in the autoclave: motor controlled by PID control, shaft with a marine anchor-shaped twin blade rotor.

Products

BSA Fraction V (Sigma A-7906) ground in a mortar and sieved. 32 to 50 μm fraction: 118.45 mg.

GÉLUCIRE® 50/02 (Gattefossé), waxy mass reduced to chips with a spatula: 452.8 mg.

Procedure

The two products are placed at the bottom of the insert. The autoclave is closed and placed under stirring with 495 rpm. The successive sequences of formation of the microspheres are then the following:

injection of $CO_2$ by equilibration with the reservoir and then the column up to the initial conditions of 24.9° C. (low T) and 99 bar.

heating of the autoclave by circulation of hot water in the jacket. The heating is regulated by PID; Duration of the heating 34 min.

maintaining equilibrium of the temperature/pressure parameters at 45.1° C. and 183 bar. These conditions are maintained for 66 min, stirring 495 rpm.

cooling by circulation of fluid in the jacket. Duration 41 min, up to: T=20° C., P=79 bar.

decompression in a buffer container to: T=25° C., atmospheric P. Duration=7 min.

The coated particles are recovered in the insert. About 150 mg thereof are recovered.

EXAMPLE 2

Microspheres of GÉLUCIRE® 50/02 Containing a Commercial Preparation of Solid Erythropoietin (HÉMAX®)

Material

Identical to that used in Example 1.

Products

HÉMAX® 2000 IU: 64 mg.

GÉLUCIRE® 50/02 (Gattefossé) waxy mass reduced to chips with a spatula: 259 mg.

Procedure

The two products are placed at the bottom of the insert. The autoclave is closed and placed under stirring with 460 rpm. The successive sequences of formation of the microspheres are then the following:

injection of $CO_2$ by equilibration with the reservoir and then the column up to the initial conditions of T=23° C. and P=100 bar.

heating of the autoclave by circulation of hot water in the jacket. The heating is regulated by PID; Duration of the heating 24 min.

stabilization of the temperature/pressure at 45° C. and 203 bar. These conditions are maintained for 65 min, stirring 460 rpm.

cooling by circulation of fluid in the jacket. Duration 49 min, to: T=17° C., P=74 bar.

decompression through vent opening to: T=25° C., atmospheric P. Duration=25 min.

recovery of the particles under a nitrogen atmosphere. 150 to 160 mg thereof are recovered.

What is claimed is:

1. Microspheres for administration by injection or by the subcutaneous or intramuscular route comprising:
   a protein active ingredient which has been coated by a coating agent by stirring in a supercritical fluid,
   wherein the coating agent is soluble in the supercritical fluid, and
   wherein the protein active ingredient and the coating agent in the microspheres are substantially free of any organic solvent.

2. The microspheres according to claim 1, wherein the microspheres exhibit a mean size from 0.1 to 150 μm.

3. The microspheres according to claim 1, wherein the protein active ingredient is from 0.5 to 50% by weight of the microspheres.

4. The microspheres according to claim 1, wherein the protein active ingredient is selected from the group consisting of parathyroid hormone related protein (parathyroid hormone related protein), growth hormone (GH), α-, β-, or γ-interferons, α- or β-erythropoietin (EPO), granulocyte colony stimulating factor (GCSF), granulocyte macrophage colony stimulating factor (GMCSF), PACAP polypeptide (pituitary adenylate cyclase activating polypeptide), vasoactive intestinal peptide (VIP), thyrotrophin releasing hormone (TRH), corticotrophin releasing hormone (CRH), arginine vasopressin (AVP), angiotensin, insulin, somatotropin, HBS antigen of hepatitis B virus, plasminogen tissue activator, coagulation factors VIII and IX, glucosylceramidase, sargramostim, lenograstin, filgrastin, interleukin-2, dornase-α, molgramostim, PEG-L-asparaginase, PEG-adenosine deaminase, hirudin, eptacog-α (human blood coagulation factor VIIa) and nerve growth factors.

5. The microspheres according to claim 4, wherein the active ingredient is α- or β-erythropoietin.

6. The microspheres according to claim 1, wherein the protein active ingredient is a peptide chosen from derivatives of luteinizing hormone releasing hormone, derivatives of somatostatin, triptorelin, bombesin, calcitonin, parathyroid hormone, gastrin releasing peptide (GRP), luteinizing hormone releasing hormone (LHRH), growth hormone releasing factor (GRF), Acetyl-Ser-Asp-Lys-Pro and amylin.

7. The microspheres according to claim 1, wherein the coating agent is selected from the group consisting of:

biodegradable polymers and copolymers of α-hydroxycarboxylic acids, poly (ε-caprolactone) and its derivatives, poly (β-hydroxybutyrate), poly(hydroxyvalerate) and (β-hydroxybutyrate-hydroxyvalerate) copolymers, polymalic acid, amphiphilic block polymers of polylactic acid-polyethylene oxide, biocompatible polymers of polyethylene glycol, polyethylene oxides, block copolymers of polyethylene oxide-polypropylene oxide, polyanhydrides, polyorthoesters, polyphosphazenes, and mixtures thereof.

8. The microspheres according to claim 1, wherein the coating agent comprises a fatty substance.

9. The microspheres according to claim 8, wherein the coating agent is a mixture of mono-, di- and triglycerides of fatty acid esters and of polyethylene glycol.

10. The microspheres according to claim 1, prepared by a process comprising:

suspending the active ingredient in the supercritical fluid with stirring, dissolving the coating agent in the supercritical fluid with stirring, modifying at least one of temperature and pressure to desolvate the coating agent in a controlled manner and cause coacervation, while stirring is maintained.

11. The microspheres according to claim 10, wherein the coating agent in the supercritical fluid has a concentration of from 1.5 to 4.5 g/l.

12. The microspheres according to claim 10, wherein the coacervation temperature is from 35 to 80° C., the coacervation pressure is from 100 to 250 $10^5$ Pa, and the stirring speed is from 200 to 1000 rpm.

13. The microspheres according to claim 10, wherein the process comprises placing an insert in an autoclave and wherein the suspending of the active ingredient and dissolving of the coating agent are carried out in the insert.

14. The microspheres according to claim 3, wherein the active ingredient is from 3 to 20% by weight of the microspheres.

15. The microspheres according to claim 4, wherein the protein active ingredient is a nerve growth factor, which is selected from the group consisting of NGF, CNTF, BDNG, FGF and GDNF.

16. The microspheres according to claim 7, wherein the biodegradable polymers and copolymers of α-hydroxycarboxylic acids comprise homopolymers and copolymers of lactic and glycolic acids.

17. The microspheres according to claim 16, wherein the biodegradable polymers and copolymers of α-hydroxycarboxylic acids comprise PLA (Poly-L-lactide) and PLGA (Poly-Lactic-co-Glycolic Acid).

18. The microspheres according to claim 8, wherein the fatty substance is selected from the group consisting of tram phospholipids, triglycerides, solid fatty acid esters and mixtures thereof.

19. The microspheres according to claim 18, wherein the phospholipids are selected from the group consisting of phosphatidylcholine, phosphatidylglycerol, diphosphatidylglycerol, dipalmitoyl-phosphatidyl-choline, dioleyl-phosphatidylethanolamine, dioleyl-phosphatidylcholine, dimyristoyl-phosphatidylglycerol, and mixtures thereof.

20. The microspheres according to claim 18, wherein the triglycerides comprise $C_8$ to $C_{12}$ triglycerides.

21. The microspheres according to claim 20, wherein the triglycerides comprise triglycerides of capric acid, caprylic acid, and mixtures thereof.

22. The microspheres according to claim 18, wherein the solid fatty acid esters comprise $C_8$ to $C_{18}$ fatty acid esters.

23. The microspheres according to claim 22, wherein the solid fatty acid esters are selected from the group consisting of ethyl palmitate, ethyl myristate, octyldodecyl myristate, and mixtures thereof.

24. The micro spheres according to claim 18, wherein the solid fatty acid esters comprise $C_8$ to $C_{12}$ fatty acid esters.

25. The microspheres according to claim 10, wherein the coating agent in the supercritical fluid has a concentration of about 2 g/l.

26. The microspheres according to claim 12, wherein the coacervation temperature is from 35 to 45° C., the coacervation pressure is from 180 to 220 $10^5$ Pa, and the stirring speed is 450 rpm.

* * * * *